United States Patent
Bik et al.

(10) Patent No.: US 8,641,967 B2
(45) Date of Patent: Feb. 4, 2014

(54) ANTI-MICROBIAL DEVICE

(75) Inventors: Russell J. Bik, Arroyo Grande, CA (US); Sean Morham, Napa, CA (US)

(73) Assignee: Applied Silver, Inc., Hayward, CA (US)

( * ) Notice: Subject to any disclaimer, the term of this patent is extended or adjusted under 35 U.S.C. 154(b) by 0 days.

(21) Appl. No.: 13/402,771

(22) Filed: Feb. 22, 2012

(65) Prior Publication Data

US 2012/0213665 A1    Aug. 23, 2012

Related U.S. Application Data

(60) Provisional application No. 61/445,979, filed on Feb. 23, 2011.

(51) Int. Cl.
  *A61L 2/16*  (2006.01)
  *A61L 2/238*  (2006.01)
  *A61L 2/24*  (2006.01)

(52) U.S. Cl.
  USPC .............................. 422/28; 210/764; 68/5 C

(58) Field of Classification Search
  USPC .................. 422/28; 210/764; 68/5 C
  See application file for complete search history.

(56) References Cited

U.S. PATENT DOCUMENTS

| | | | | |
|---|---|---|---|---|
| 3,751,885 A * | 8/1973 | McNeely | ...................... | 96/242 |
| 4,145,291 A * | 3/1979 | Console et al. | ................ | 210/232 |
| 4,696,742 A * | 9/1987 | Shimazaki | ..................... | 210/287 |
| 4,933,870 A * | 6/1990 | Chang | ............................ | 700/268 |
| 5,190,659 A * | 3/1993 | Wang et al. | ................... | 210/663 |
| 5,765,403 A * | 6/1998 | Lincoln et al. | ................. | 68/13 R |
| 5,843,284 A * | 12/1998 | Waters et al. | ................. | 196/46.1 |
| 6,524,540 B1 | 2/2003 | Heinig, Jr. | | |
| 6,634,048 B1 * | 10/2003 | Hornung et al. | ................... | 8/158 |
| 7,807,661 B2 | 10/2010 | Ylitalo et al. | | |
| 2001/0049846 A1 * | 12/2001 | Guzzi et al. | ........................ | 8/158 |
| 2003/0230122 A1 * | 12/2003 | Lee | .................................. | 68/58 |
| 2004/0214495 A1 | 10/2004 | Foss et al. | | |
| 2005/0019568 A1 | 1/2005 | Foss et al. | | |
| 2005/0155939 A1 | 7/2005 | Stadelmann | | |
| 2006/0110258 A1 * | 5/2006 | Iimura et al. | ..................... | 417/18 |
| 2007/0045176 A1 | 3/2007 | Chandra et al. | | |
| 2007/0243380 A1 | 10/2007 | Vegad et al. | | |
| 2007/0243781 A1 | 10/2007 | Chou | | |
| 2008/0023385 A1 | 1/2008 | Baker, Jr. et al. | | |
| 2008/0041117 A1 * | 2/2008 | Lee | .............................. | 68/17 R |
| 2008/0085326 A1 | 4/2008 | Ruan | | |
| 2008/0217807 A1 | 9/2008 | Lee et al. | | |
| 2008/0302713 A1 * | 12/2008 | Patrick | .......................... | 210/234 |
| 2009/0104239 A1 * | 4/2009 | Parsons et al. | ................ | 424/409 |
| 2009/0181592 A1 | 7/2009 | Dugan | | |
| 2010/0050872 A1 | 3/2010 | Lee | | |
| 2010/0102002 A1 | 4/2010 | O'Brien et al. | | |

\* cited by examiner

*Primary Examiner* — Sean E Conley
*Assistant Examiner* — Donald Spamer
(74) *Attorney, Agent, or Firm* — Felix L. Fischer

(57) ABSTRACT

Under electronic monitoring and control, fluids flow into a fluid diffusion device 9 to form a fluid combination. The fluid combination has corrosive properties as it flows into an anti-microbial canister 8 housing a roll 4 of anti-microbial metallic coated substrate 1, support frame 2, and porous body 3. The fluid combination corrodes the anti-microbial metallic coated substrate 1 located inside the anti-microbial canister 8. Upon exiting the anti-microbial canister 8, the fluid combination contains dissolved metal and is a liquid anti-microbial agent. Monitors throughout the system ensure the anti-microbial agent is being produced at the desired level and rate as it exits into its application.

14 Claims, 13 Drawing Sheets

ANTI-MICROBIAL DEVICE

REFERENCE TO RELATED APPLICATIONS

This application claims priority of U.S. Provisional Patent Application Ser. No. 61/445,979 filed on Feb. 23, 2011 entitled ANTI-MICROBIAL DEVICE the disclosure of which is incorporated herein by reference.

BACKGROUND OF THE INVENTION

1. Field

The present invention is in the technical field of anti-microbial treatment. More particularly, the present invention provides a system employing a metallic source substrate supported in a fluid combination flow with controlled fluid diffusion inducing metallic ion and microscopic particle generation in desired concentration, for entrainment in the flow, for use in anti-microbial treatments.

2. Related Art

Shortcomings of existing anti-microbial treatments can lead to the spread of infection through direct contact, airborne disease and waterborne disease. These diseases can be acquired by their victims from contacting contaminated surfaces, breathing air containing pathogens, or drinking pathogen containing water. Contaminated drinking water especially affects populations of second world and third world countries. The lack of inexpensive means to rid drinking water of harmful living microbes results in widespread illness and death in second world and third world countries. Similarly, contamination of fabrics or linens in uniforms, surgical scrubs, sheets, blankets, napkins, table cloths and similar materials by microbial pathogens can contribute to spread of disease.

Previous anti-microbial treatments require concentrated chemicals which are potentially or actually harmful to people and the environment. Such anti-microbial treatments also do not provide a lasting anti-microbial effect after the treatment has been administered. Existing anti-microbial treatments can also lead to immunization of evolved pathogens to the respective treatment. Such immunization of evolved pathogens can result in infections which cannot be treated with the conventional treatments that caused the pathogens to become immune.

Enterprises which specifically have problems with the spread of infectious diseases include, but are not limited to: the cruise line industry, hotel and gaming, professional sports teams, health and fitness clubs, nursing homes, and hospitals. Healthcare facilities currently have a growing problem with immunized pathogens being virtually untreatable with conventional methods. With such hospital infections, the harmful microbes are often carried in the linens and clothing provided by the hospital. Once hospital linens have been laundered and treated, they are susceptible to recontamination by microbes and pathogens. Pathogens carried by these linens can infect hospital patients and even cause death.

It is therefore desirable to provide an anti-microbial treatment system which may be employed directly in water supply systems to provide efficacious anti-microbial action.

SUMMARY OF THE INVENTION

The present invention is a device which releases a lasting, metallic, anti-microbial agent to which no known pathogens can become immune. Embodiments of the anti-microbial device disclosed herein incorporate a metallic coated substrate suspended with a support frame and a porous body positioned with respect to the substrate for intimate contact of turbulated fluid combination flow with the substrate in the porous body. A housing contains the substrate, support frame and porous body and has an inlet and outlet for the fluid combination. A fluid diffusion device is connected upstream of the housing inlet and receives one fluid at a fluid inlet and a different fluid at a diffusion inlet. Control of flow of separate fluids into the fluid diffusion device maximizes generation of anti-microbial metallic ions and/or microscopic particles from the substrate contained within the housing.

BRIEF DESCRIPTION OF THE DRAWINGS

These and other features and advantages of the present invention will be better understood by reference to the following detailed description of exemplary embodiments when considered in connection with the accompanying drawings wherein.

DETAILED DESCRIPTION OF THE INVENTION

Figure 1:
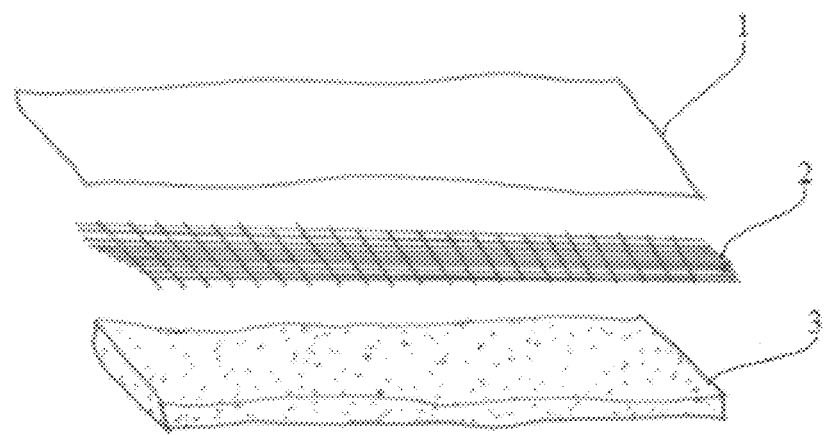
FIG. 1 is an exploded isometric view of a metallic anti-microbial coated substrate, support frame and porous body.

Describing an embodiment of the invention in more detail with reference to the drawings, FIG. 1 shows an anti-microbial metallic coated substrate 1 above a support frame 2. A porous body 3 shown at the bottom of FIG. 1 is used to suspend and maintain separation of the anti-microbial metallic coated substrate 1 and the support frame 2 in a rolled configuration. The anti-microbial metallic coated substrate 1, support frame 2 and porous body 3 are rolled in a helix forming continuous expanding layers, referred to herein as a roll 4, as shown in FIG. 2.

Figure 2:
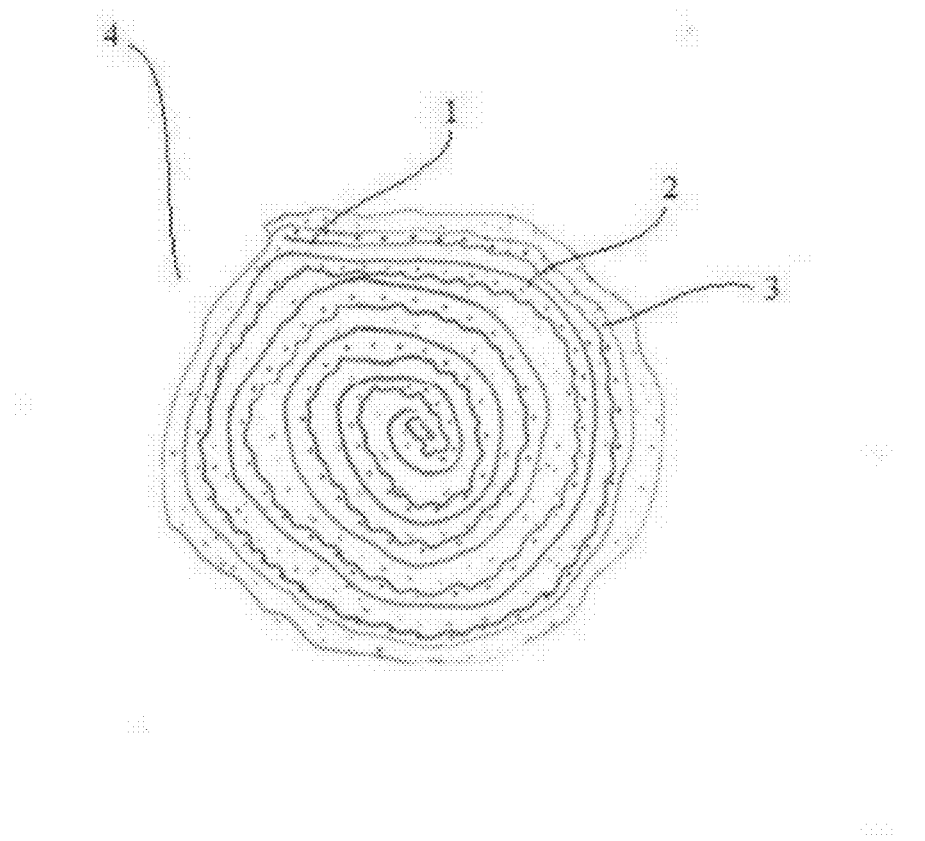
FIG. 2 is an end view of the anti-microbial metallic coated substrate, support frame and porous body rolled into the orientation for insertion into the central cylinder used in the present invention.
Figure 3:
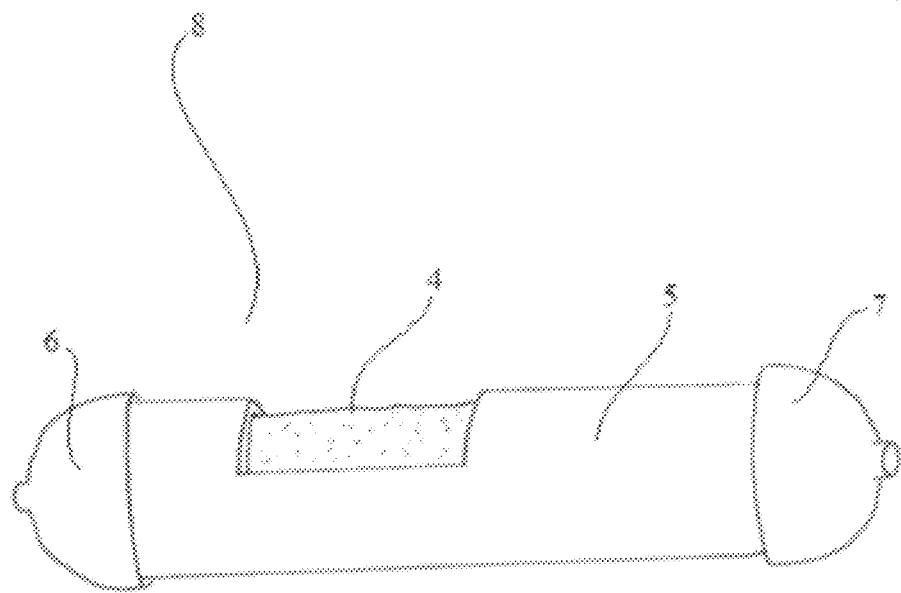
FIG. 3 is a side view with a cut away of the central cylinder used to house the rolled combination of elements.

FIG. 3 shows a central cylinder 5 in which the roll 4 shown in FIG. 2 is inserted. The central cylinder 5 houses the roll 4 while allowing fluids to enter and exit the central cylinder 5 through end caps 6 and 7. The roll 4 inserted into the central cylinder 5 and held in place by inlet end cap 6 and outlet end cap 7 as an assembly referred to as the anti-microbial canister 8.

Figure 4:
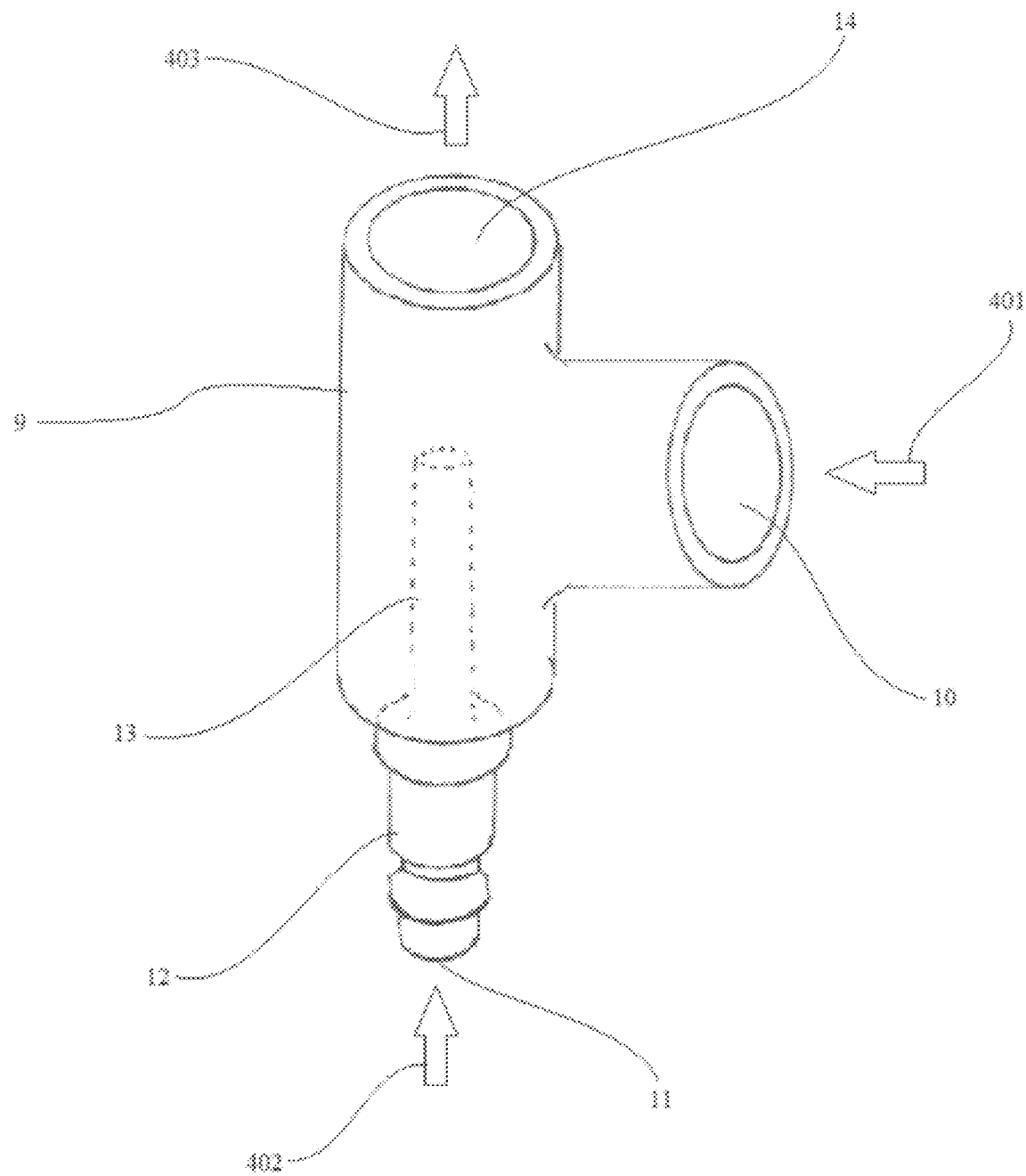
FIG. 4 is a three quarters view of a fluid diffusion sub-assembly which is used in the present invention.

FIG. 4 shows a fluid diffusion device 9 used in combination with the canister 8 in the embodiment shown in the drawings to be described in greater detail subsequently. The fluid diffusion device 9 allows a first fluid (fluid #1) to flow into a fluid inlet 10 in the direction of arrow 401 and through a central cavity 404 in a main body 405. A second fluid (fluid #2) is injected through a fluid diffusion inlet 11 and barb 12 in the direction of arrow 402. Once through the barb 12, the second fluid enters a connected diffuser 13 which is oriented parallel to the main body 405 of the fluid diffusion device 9. The second fluid acts as a turbulating agent and diffuses into first fluid in the cavity 404 of the main body 405 to form a fluid combination. The fluid combination exits the fluid diffusion device 9 through the fluid combination outlet 14 in the direction of arrow 403. The fluid diffusion device 9 is connected to the canister 8 such that the fluid combination flows then through the anti-microbial canister 8 as will be described in greater detail subsequently. Fluid #1 and fluid #2 can be any fluid combination, however, because fluid #1 is most commonly water and fluid #2 is most commonly air, the specific embodiments of the present invention will be described using these specific exemplary fluids. In certain embodiments, gaseous oxygen could be substituted for air as the turbulating agent for enhanced oxygenation of the water.

Figure 5:
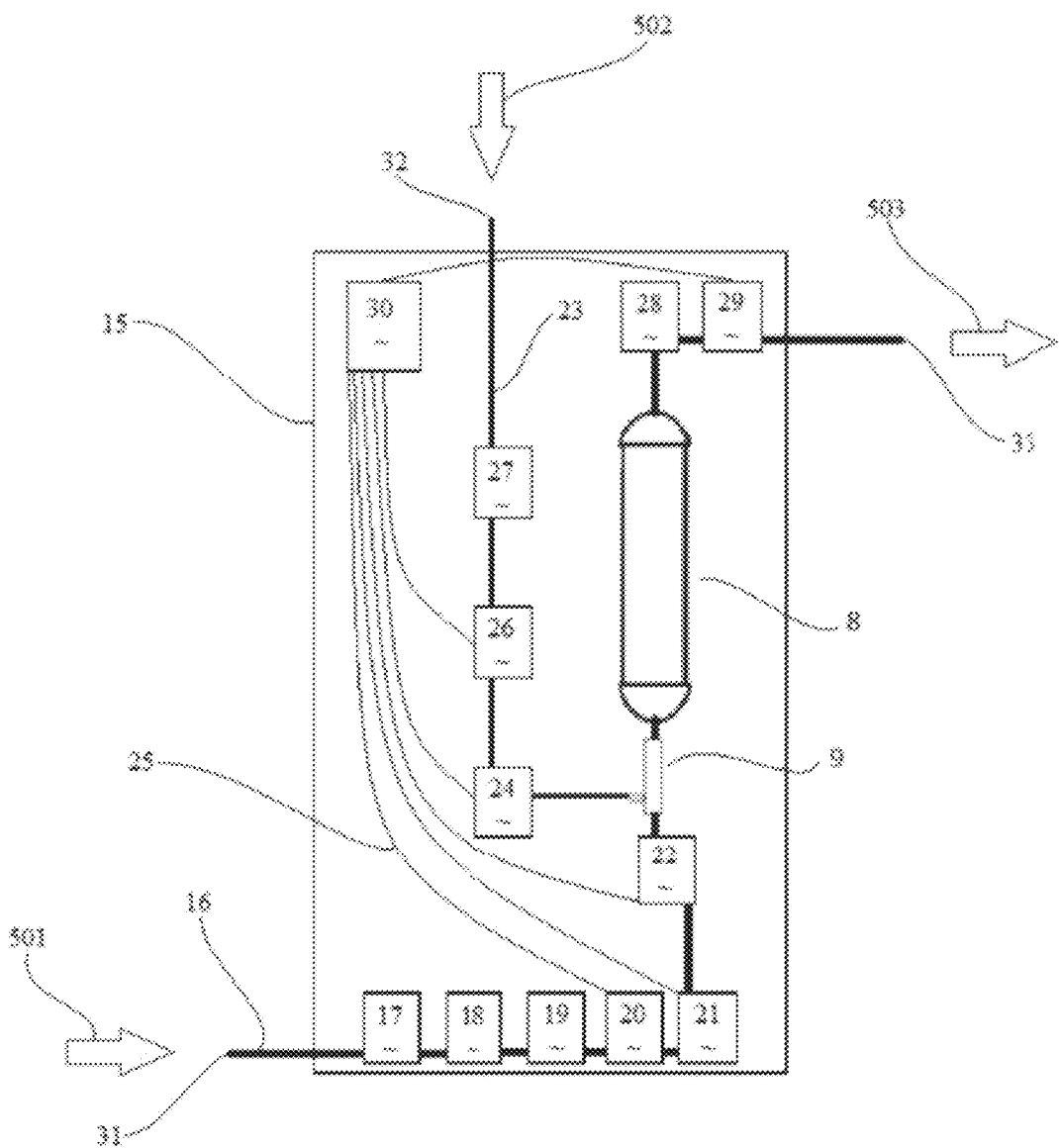
FIG. 5 is a system flow diagram of and exemplary embodiment of the electronic control and monitoring system, separate fluid lines, fluid diffusion sub-assembly and anti-microbial canister.

FIG. 5 shows a system flow diagram of an embodiment of the canister 8 and fluid diffusion device 9 with an electronic control and monitoring system. FIG. 5 shows seven electronic devices, three mechanical regulators, the anti-microbial canister 8, and the fluid diffusion device 9, a manual water shut off 17, a water filter 19, water inlet 31, air inlet 32, and the anti-microbial fluid combination outlet 33. The seven electronic devices which will be described in greater detail subsequently are: an electronics module 30, which is a programmable device such as a microprocessor having software or firmware for specific INITIALIZATION; IDLE; PROCESS; and SHUTDOWN sequences, a solenoid water shut off valve 20, a water temperature sensor 21, a water pressure sensor 22, a air pressure sensor 24, a solenoid air shut off valve 26, and a flow sensor 29.

The electronics module 30 has a power switch 501, manual start button 502, manual stop button 503, cooling fans 504, LCD display 505, and Manual Mode/Automatic Mode switch 506. The electronics module 30 also has wired and/or wireless connection 507 to local area internet networks to send data to any remote monitoring system with an internet connection. This internet capability also allows the system to be controlled wirelessly over the internet. For example, the system can be turned on and off over the interact and the allowable parameters for sensor detection can be adjusted over the internet. Because, the electronics module 30 can be controlled using the various buttons and switches on the electronics module 30 itself, or remotely though a local area network, the operator can control and monitor the present invention on site or offsite. The programs for the electronics module 30 will be detailed fully using software flow diagrams as seen in FIG. 6, FIG. 7, FIG. 8, FIG. 9, and FIG. 10. The compilation of the electronics module programs provides the electronic control and monitoring system software. If the electronics module 30 receives electronic communication from one of the sensors, the electronic control and monitoring system software can be programmed to send signals or alerts to the operator via the wireless connection 507 or as messages to the LCD 504. The electronic control and monitoring system software also continuously togs data on system events and on received transmissions from the multiple sensors.

The solenoid water shut off valve 20, is used to start and stop water flow entering through inlet 31 as shown by arrow 508 through the system. The water temperature sensor 21 communicates electronically with the electronics module 30 in order to enable the electronic control and monitoring system software to log data or send an alert to the operator if water temperature deviates from a desired range. The water pressure sensor 22 communicates electronically with the electronics module 30 in order to enable the electronic control and monitoring system software to log data or send an alert to the operator if water pressure deviates from a desired range. The air pressure sensor 24 communicates electronically with the electronics module 30 in order to enable the electronic control and monitoring system software to log data or send an alert to the operator if air pressure deviates from a desired range. The solenoid air shut off 23 is used by the electronics module to start and stop air flow through the system entering at inlet 32 as indicated by arrow 509. The flow sensor 29 determines outlet flow from the system through outlet 33 as shown by arrow 510 and communicates electronically with the electronics module in order to enable the electronic control and monitoring system software to log data or send an alert to the operator if flow rate deviates from a desired range. The three mechanical regulators are: a water pressure regulator 18, an air pressure regulator 27, and a flow reducer 28.

The seven electronic devices, three mechanical regulators, the anti-microbial canister 8, the diffusion device 9, the manual water shut off 17, and water filter 19 are interconnected by the water line 16 and air line 23. The seven electronic devices are connected to the electronics module 30 by the electronic wiring 25. The electronic devices, mechanical devices, and the interconnecting plumbing lines and wires shown are all mounted to a mounting surface 15. An example set of parameters for the electronic control and monitoring system software might be programmed to monitor and control are the following: 140° F. water temperature, 15 psi of water pressure, 25 psi of air pressure, 2 gallon per minute (GPM) of flow rate, all with an acceptance range of within +/−15% before alerting the operator via warning and/or error messages displayed on the LCD screen on the electronics module 30 or through alerts transmitted aver the local area network connection when the electronic control and monitoring system transmits a status report.

Figure 6:
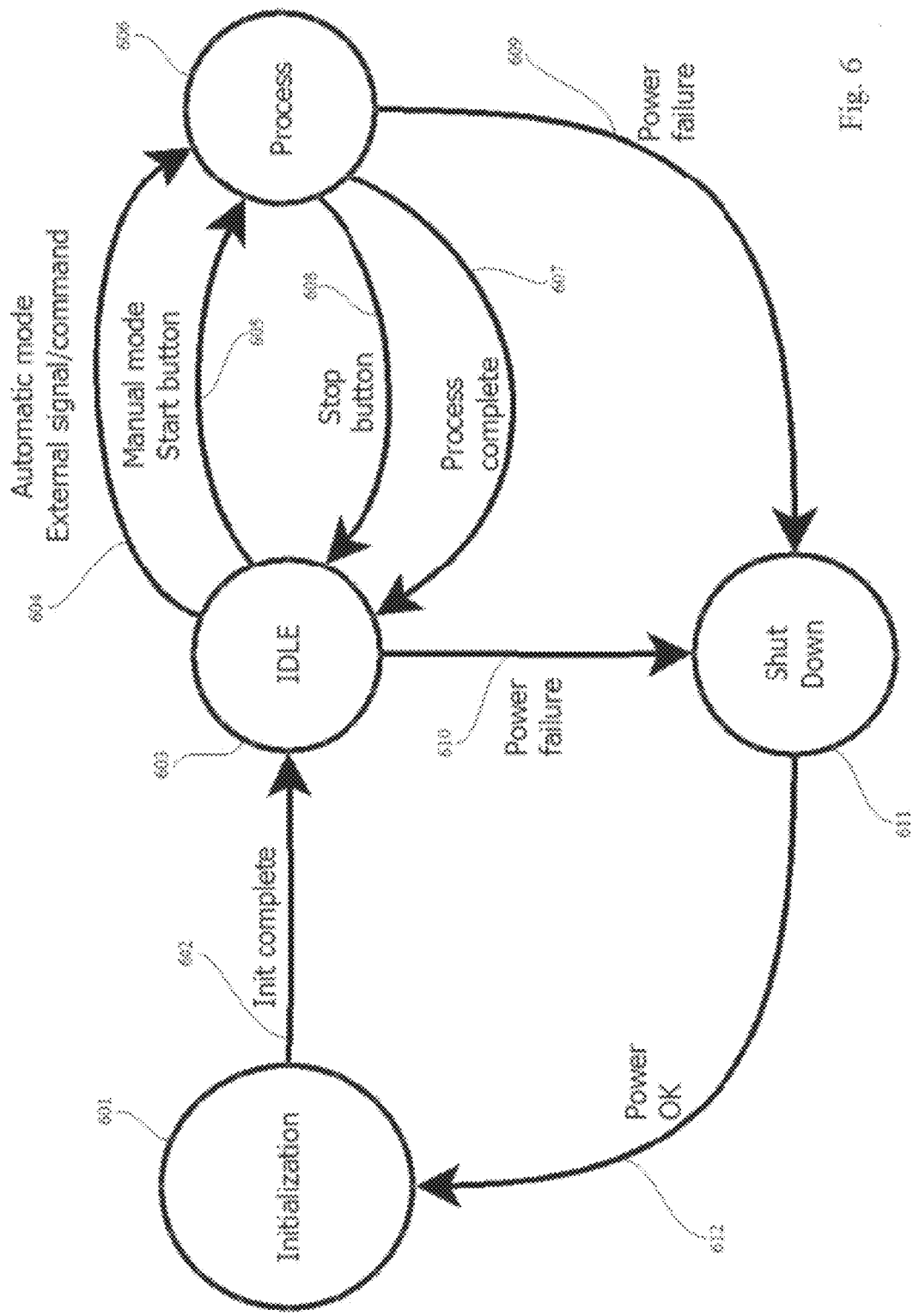
FIG. 6 is a general firmware flow diagram for the electronic control and monitoring system which includes the following major states and modes: INITIALIZATION, IDLE, PROCESS and SHUTDOWN.

FIG. 6 shows a firmware flow diagram which the electronics module 30 is programmed to follow. Each circle in FIG. 6 represents a step in the system's electronic control and monitoring system software and each arrow represents an event, falling into one of two categories an occurrence or a command. Upon an event, the electronic control and monitoring system software moves to another step. Beginning in the top left corner of the flow diagram and following the event arrows: the INITIALIZATION 601 sequence commences when the electronics module 30 is powered on. If INITIALIZATION 601 is successful as signified by Init complete 602, the system enters IDLE 603 state. Two options of state exist for IDLE 603 state; they are Manual mode and Automatic mode. Once in IDLE 603 mode, one of three events can occur, two of which are the commands: External Signal/command 604 and Start button 605 function according to whether the operator has selected Manual mode or Automatic mode using switch 506 on the electronics module 30. For example, in Automatic mode, an external signal from an outside device is required to advance the system from IDLE 603 state to PROCESS 606 mode whereas in Manual mode, the pressing of start button 502 on the electronics module 30 signals the Start button 605 command and advances the system from IDLE 603 state to PROCESS 606 mode. In either mode, signals from the other mode are not recognized. The third possible event is an occurrence, Power failure 610, which ultimately sends the system into a SHUTDOWN 611 sequence. If the system advances into PROCESS 606 mode, the following two commands can move the system from PROCESS 606 mode back to IDLE 603 state: Stop button 608 command (Manual mode) and Process complete command 607 (Automatic mode) The Stop button 608 command Process complete 607 command are inverse events to the Start button 605 command and External signal/command 604 described above. In order for the system to move directly from PROCESS 606 mode to SHUTDOWN 611 sequence, a Power failure 610 must occur. Once the SHUTDOWN 611 sequence is complete, power must be restored, Power OK 612, in order for the system to return to INITIALIZATION 601, at which point the entire process will restart.

Figure 7:
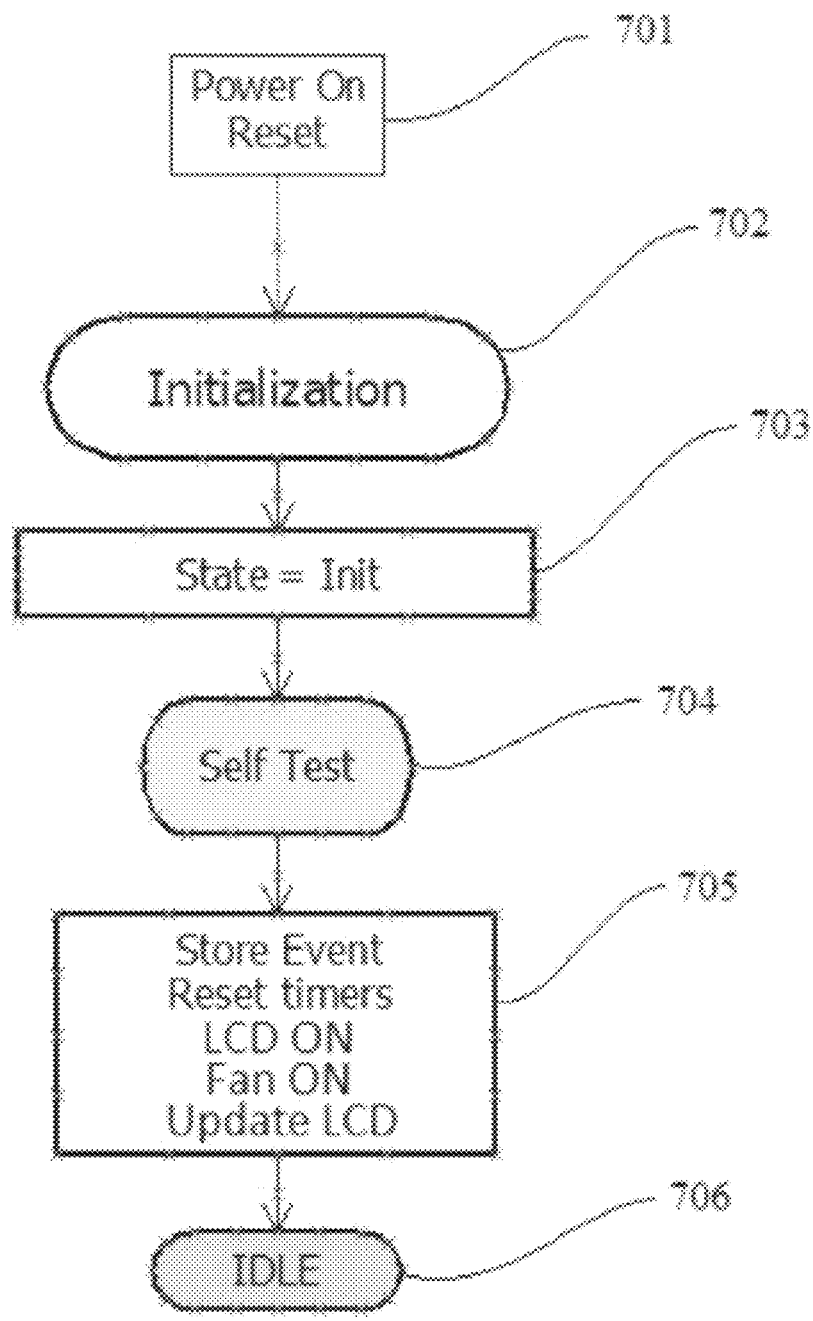
FIG. 7 is a software flow diagram specific to when the electronic control and monitoring system enters INITIALIZATION sequence.

FIG. 7 shows a detailed flow diagram of the sequence that the electronic control and monitoring system software carries out to advance from INITIALIZATION 601 to IDLE 603 state. The flow diagram flows from top to bottom. Each shape represents a step in the sequence. Each arrow represents advancement from one step to the next. INITIALIZATION begins when power is supplied, Power On/reset 701, to the electronics module 30. Upon receiving power, the next step is for the electronic control and monitoring system to define its state–State=Init 703. Once INITIALIZATION 601 has been started, a Self Test 704 checks system functions including detection of pressures, temperatures, and flow-rate. Once the Self Test 704 is completed, IDLE is logged to non-volatile memory, timers are reset for IDLE state, the LCD is turned on if not already on, actual values of the desired parameters are displayed on the LCD, and the fan is turned on 705. At this point the system enters IDLE 603 state.

Figure 8:
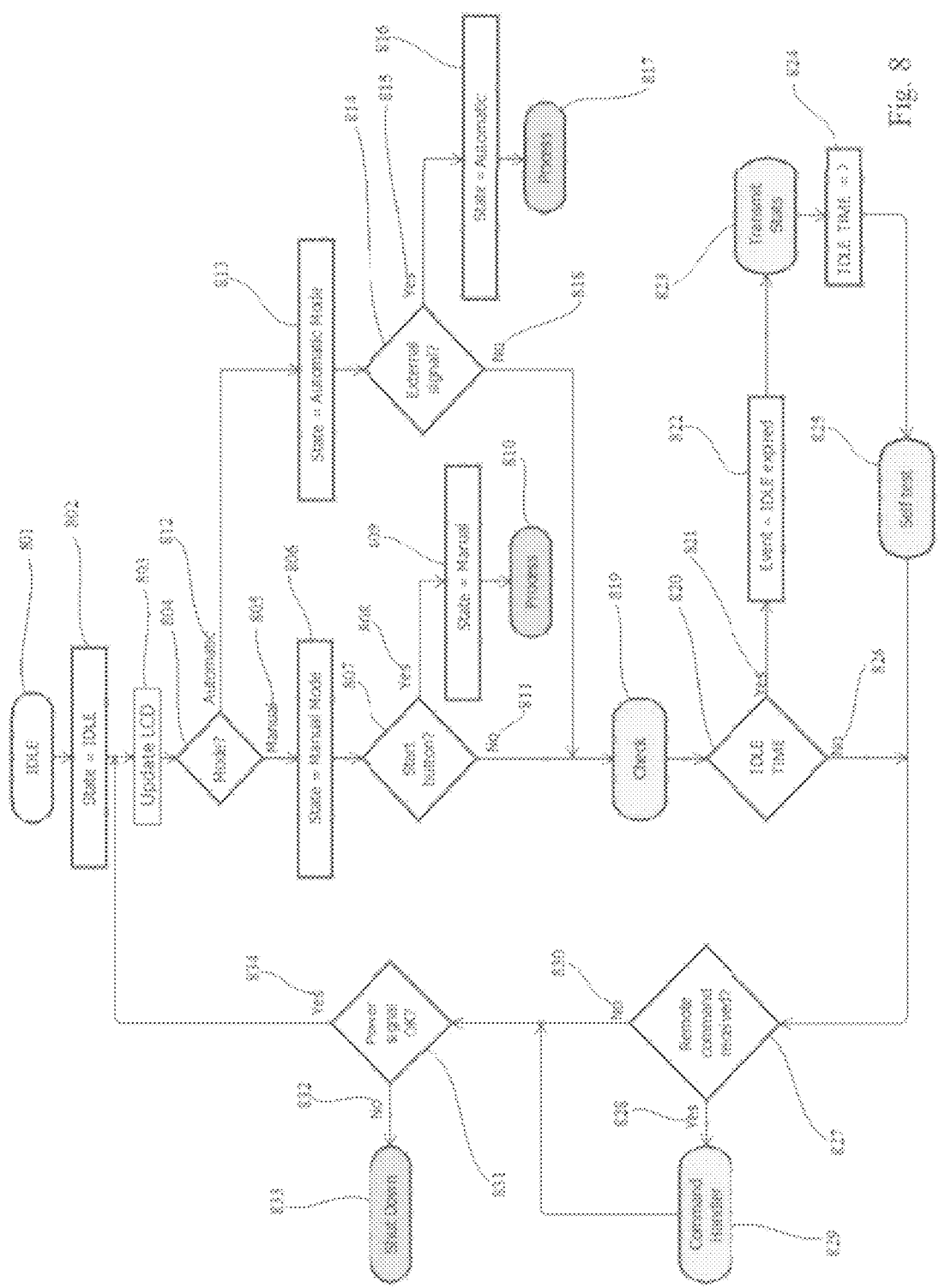
FIG. 8 is a software flow diagram specific to when the electronic control and monitoring system enters the IDLE state.

FIG. 8 shows a detailed flow diagram of all possible sequences of events to advance the electronic control and monitoring system software from IDLE 603 state to PROCESS 606 mode or SHUTDOWN 611 sequence. Each shape represents a step in each possible sequence. Each arrow represents advancement from one step to the next. Beginning at the top center of the flow diagram at IDLE 603 state, the next step is the IDLE state defined and set by the electronic control and monitoring system, as signified by State=IDLE 802. The next step is to Update the LCD 803 and following this, the a mode determination 804 is made of either Manual Mode 805 or Automatic Mode 812 which has been established by the operator using the Manual Mode/Automatic Mode switch on the electronics module 30. First, Manual 805 selection will be described. If Manual Mode is selected on the electronics module 30 switch, the electronic control and monitoring system software defines its state as Manual Mode 806. Next the Start button on the electronics module 30 is monitored 807 and if pressed by the operator 808 advances the system to the sub-state Manual 809. Once this state is confirmed by the electronic control and monitoring system software, PROCESS 606 mode is initiated. If the start button is not pressed 811, the system checks periodically for a specified number of seconds, as signified by Check 819. If the start button is not pressed 821 within the specified IDLE TIME 820, the event IDLE expired 822 is logged to non-volatile memory and that data is sent to off-site servers through a local area network 823 and the operator can be alerted, IDLE TIME is reset to zero 824 and Self Test 825 is conducted. After Self Test 825, the system returns to the same point in the sequence as if the idle time had not expired 826. In the next step, the electronic control and monitoring system software looks for Remote command 827 to be received. If Remote command is received 828, the Command Handler in the electronic control and monitoring system interprets and acts upon the Remote command 829 and returns to the same point in the sequence as if no Remote command was received 830. The next step is for the electronics control and monitoring system to check for Power signal 831. If Power signal is not OK 832, SHUTDOWN 611 sequence initiates. If Power signal is OK 834, the electronic control and monitoring system returns to the top level state=IDLE 802.

Now Automatic 813 state will be described. If the Manual Mode/Automatic Mode switch on the electronics module 30 is switched to Automatic Mode 812 while the system is in IDLE 801 mode, the electronic control and monitoring system software defines its state as Automatic Mode 813. Once Automatic Mode 813 state has been established, the system looks for an External signal 814. If an External signal is sensed 815, the sub-state, Automatic 816, is established by the electronic control and monitoring system software and PROCESS 606 mode is initiated. If no external signal is sensed 818 then the system returns to Check 819. If no External signals are received during Check, the electronic control and monitoring system proceeds to IDLE TIME 820 and sequenced as previously described.

Figure 9:
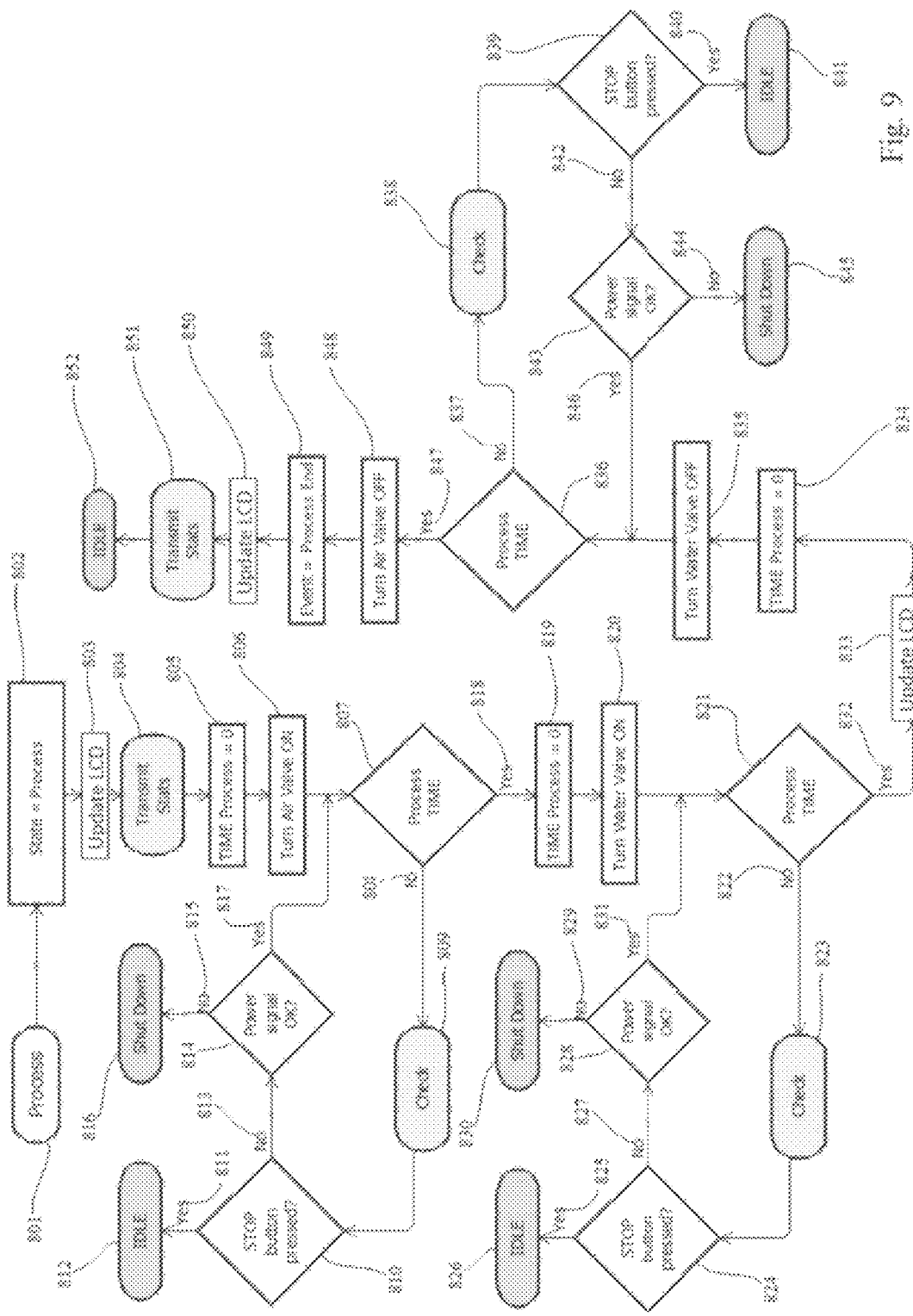
FIG. 9 is a software flow diagram specific to when the electronic control and monitoring system enters PROCESS mode.

FIG. 9 shows a detailed software flow diagram of all possible sequences that can advance the electronics control and monitoring system software from PROCESS 606 mode to IDLE 603 state or SHUTDOWN 611 sequence. Each shape represents a step in each possible sequence. Each arrow represents advancement from one step to the next. Beginning at the top left-center of the flow diagram at PROCESS 606 mode, the first step is the PROCESS mode defined and set by the electronic control and monitoring system software, as signified by State=Process 802. Once the Process state has been established, the LCD is updated 803 and the electronic control and monitoring system software will log the event to non-volatile memory and send it through a local area network to off-site servers and alert the operator if necessary, as signified by Transmit Stats 804. TIME Process is then set to zero, as signified by TIME Process=0 805, after which the electronic control and monitoring system opens the solenoid air shutoff valve 26 as signified by the Turn Air Valve On 806 step. Advancements within the process from one step to the next are referenced against time; therefore timing in the cycle is checked as signified by Process TIME 807. If time is not reset to zero 808, as signified by TIME Process=0 819 and the solenoid water shutoff valve 20 is not opened within the specified Process TIME 807, the system enters a check loop. Check loop defined: time is checked periodically for a predetermined number of counts, as signified by Check 809. If the STOP button 810 is pressed 811 on the electronics module 30, the system returns to IDLE state 603; if not 813, power is checked as signified by Power signal OK? 814. If power is not confirmed within a programmed period 815, the system triggers SHUTDOWN 611 sequence. If power is confirmed 817, the system returns to Process TIME 807 and Check 807 is complete. If time is reset to zero, as signified by TIME Process=0 819, and the solenoid water shutoff valve 20 is actuated, as signified by Turn Water Valve ON 820 the timing of the cycle is checked again, as signified by Process TIME 821 and if timing cannot be confirmed, the system enters Check 823. If the STOP button 824 is pressed 825 on the electronics module 30, the system returns to IDLE state 603; if not 827, power is checked as signified by Power signal OK? 828. If power is not confirmed within a programmed period 829, the system triggers SHUTDOWN 611 sequence. If power is confirmed 831, the system returns to Process TIME 821 and check loop is complete. If timing is confirmed 832, the LCD is updated 833, and time is reset 834. Next the solenoid water valve is actuated 835. Process timing is checked 836. If timing is not correct 837, the system enters a check loop, Check 838. If the STOP button 839 is pressed 840 on the electronics module 30, the system returns to IDLE state 603; if not 842, power is checked as signified by Power signal OK? 843. If power is not confirmed within a programmed period 844, the system triggers SHUTDOWN 611 sequence. If power is confirmed 846, the system returns to Process TIME 836 and the check loop is complete. If timing is correct 847, the solenoid air shutoff valve 26 is closed as signified by Turn Air Valve OFF 848. Following the closure of the solenoid air shutoff valve 26, the PROCESS is logged as an event to non-volatile memory as signified by Event=Process End 849. Once logged, the event is displayed on the 850. Next, this data is sent over the local area network to off-site servers, as signified by Transmit Stats 851. An operator is alerted if the transmitted stats deviate far enough from desired parameters. The system then returns to IDLE 603 state.

Figure 10:
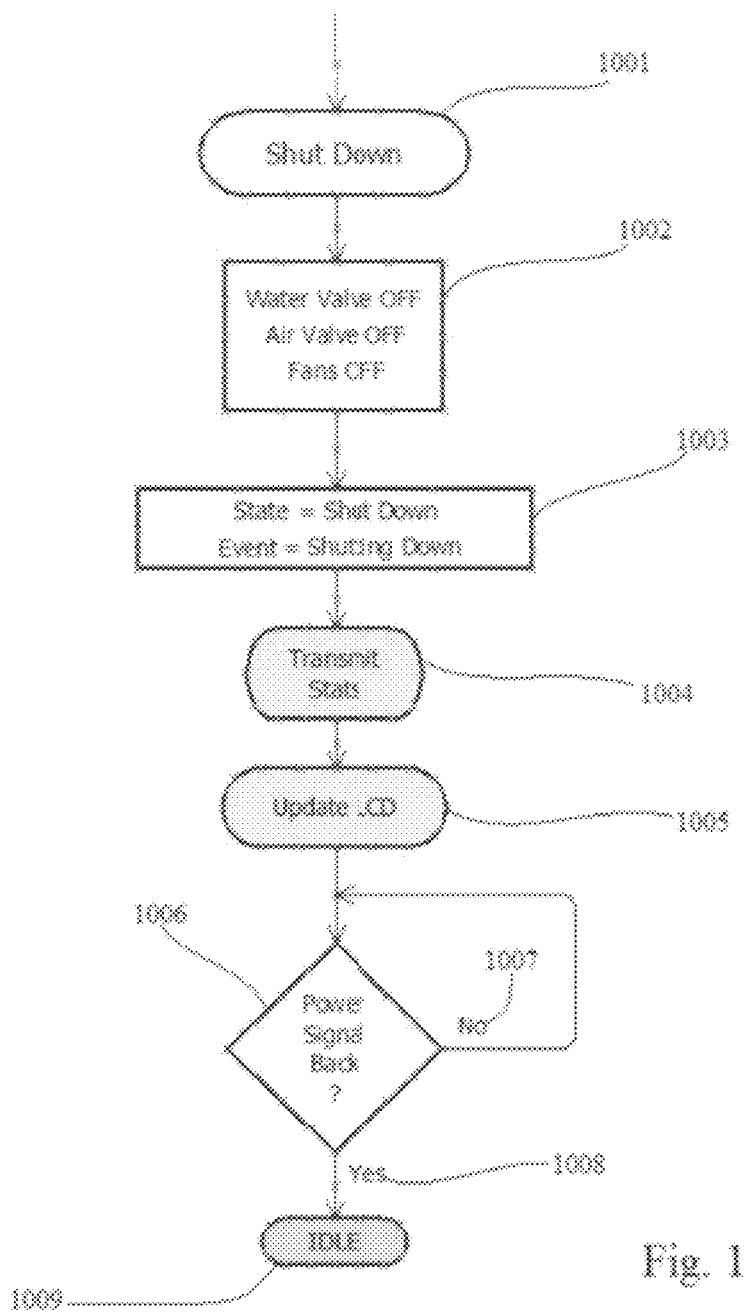
FIG. 10 is a software flow diagram specific to when the electronic control and monitoring system enters the SHUTDOWN state.

FIG. 10 shows a detailed software flow diagram of the electronic control and monitoring system advancing from SHUTDOWN 611 sequence to IDLE 603 state. Once SHUTDOWN 611 sequence has been initiated, the next step is for the electronic control and monitoring system software to dose the solenoid water shutoff valve 20, solenoid air shutoff valve 26, and turn off the cooling fans inside the electronics module 30, all of which are signified by: Water Valve OFF, Air Valve OFF, and Fans OFF, respectively 1002. Once the necessary components are turned off, Shut Down state is established. In response to the establishment of Shut Down state, the event Shutting Down is logged to non-volatile memory as signified by State=Shut Down and Event=Shutting Down, respectively 1003. The logged even is then sent through a local area network to off-site servers, as signified by Transmit Stats 1004 at the request of the operator, the system can send an alert when it loses power. The next step updates the LCD screen on the electronics module 30 as signified by Update LCD 1005. The LCD update can display alerts for the operator. Next the power is checked as signified by Power Signal Back? 1006. If power requirements are not met 1007, the system remains powerless until power returns. If power requirements are met 1008 the system enters IDLE 603 state.

Figure 11:
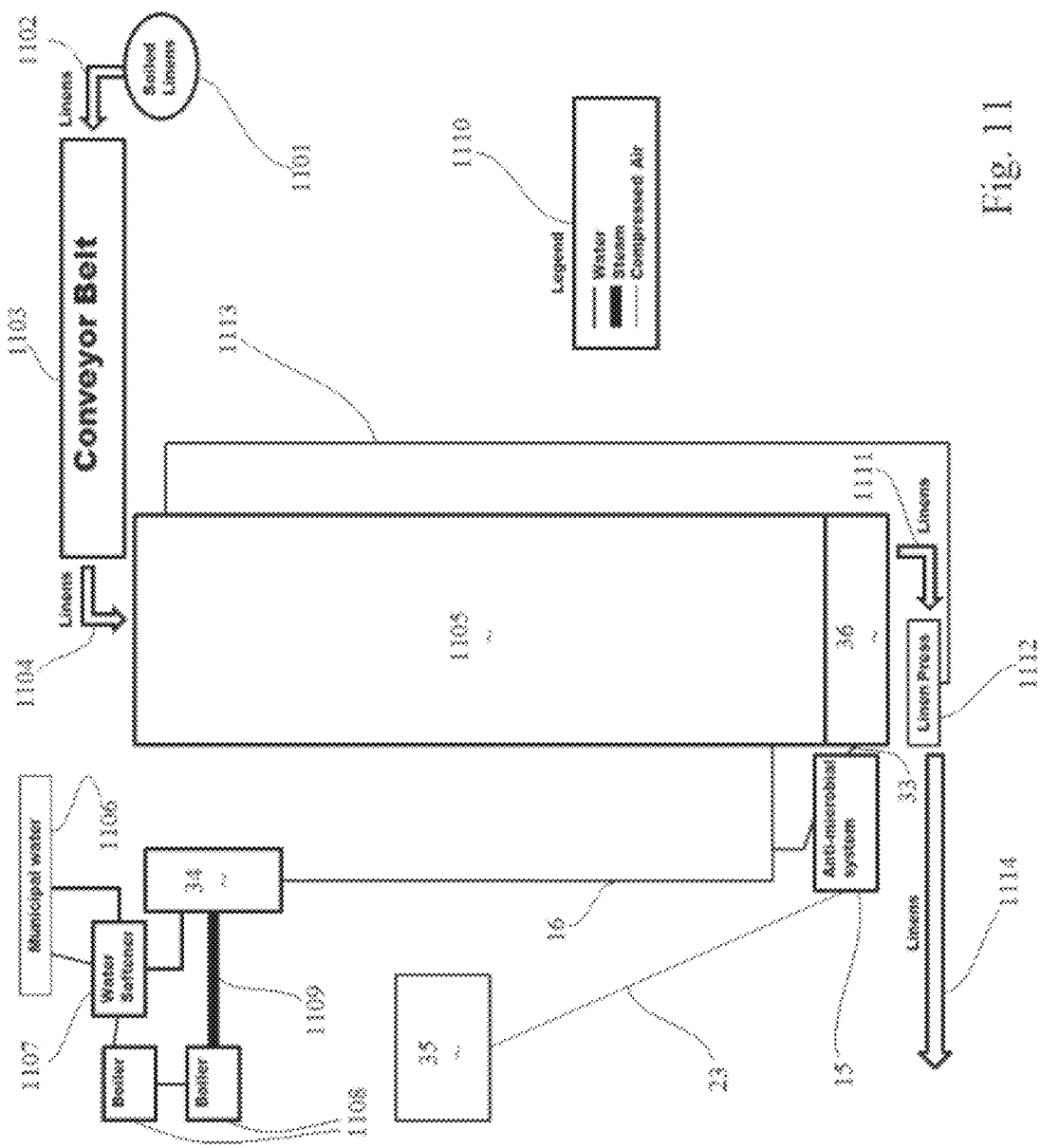
FIG. 11 is a schematic representation of an industrial washing system showing placement of the anti-microbial device for use with a Continuous Batch Washer (CBW)

An example integration of the described embodiments into another system is described in more detail with reference to FIG. 11 which shows a schematic of an industrial laundry facility. The washing machine may have multiple modules, thereby known as a Continuous Batch Washer (CBW). FIG. 11 depicts an instance where the present invention is integrated into a CBW process. Linens enter the system soiled 1101 in batches of several hundred pounds and are transferred 1102 manually by plant workers to a conveyor belt 1103 that carries them to an elevated height where they are then gravity fed 1104 into the CBW. Water, Steam, and Compressed Air lines are defined in the schematic legend 1110. The most effective integration of the present invention into this particular example of an industrial laundry facility is represented in FIG. 11 through placement of the waterline 16 and anti-microbial fluid combination outlet 33 which the example embodiment uses to inject the anti-microbial agent into the CBW rinse module 36. The example embodiment from FIG. 5 is shown integrated into the industrial system as the mounting surface 15 through its connection with hot water source 34, pressurized air source 35 and the CBW rinse module 36. The hot water source 34 receives municipal water 1106 which is conditioned by a resin based, ion exchange, water softening system 1107 and is heated using multiple boilers 1108. The water line 16 connects the municipal water source 1106, water softener 1107, boilers 1108, hot water source 34, CBW wash modules 1105 and delivers water to the present invention 15 and the anti-microbial fluid combination outlet 33 delivers the anti-microbial agent into the CBW rinse module 36. Once the linens have been treated with the anti-microbial agent in the CBW rinse module 36, they are automatically loaded 1111 into a linen press 1112, which presses excess rinse water out of the linens. That pressed water is recycled back into the beginning of the CBW system through rinse water recycle line 1113. The rinse water recycle line 1113 is important to note because it reintroduces the anti-microbial agent into the beginning of the wash cycle. Upon exiting the press 1114, the linens may enter dryers or other machines within the laundry facility.

Figure 12:
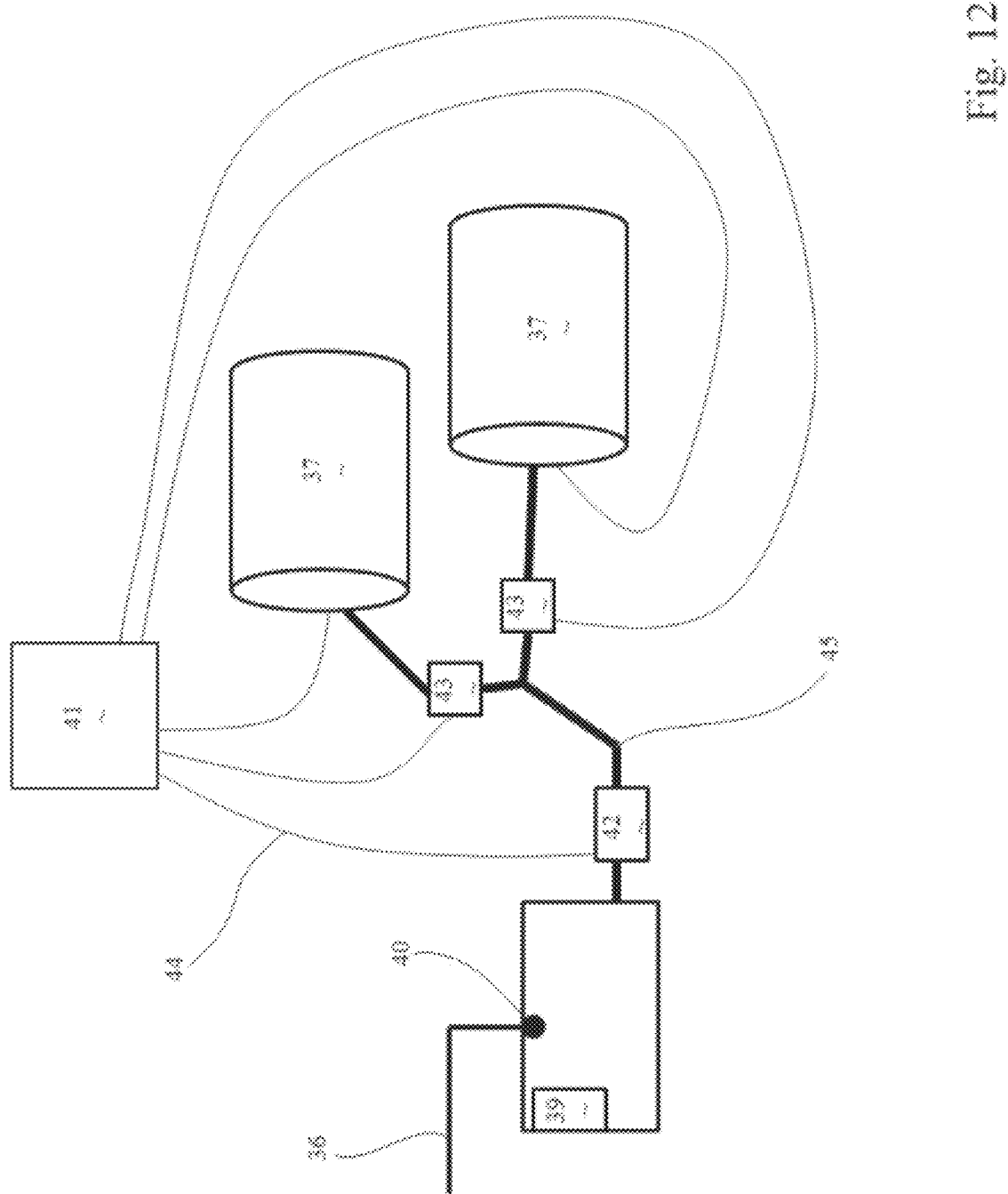
FIG. 12 is a schematic view of a set of auxiliary components which are used to collect and dispense the anti-microbial solutions for textile treatment (i) in Conventional Washer-Extractors (CWE) or (ii) when the demand flow rate of any form of a CBW or CWE exceeds the output flow rate of the anti-microbial device; and, FIG. 13 is a schematic view of a simplified embodiment.

If the washing device does not have multiple modules, but rather a single module, possibly with different compartments, it is known as a Conventional Washer-Extractor (CAVE) 37 and represented in FIG. 12. Additionally, FIG. 12 depicts an anti-microbial solution reservoir 38 which contains a float level sensor 39 that electronically signals the electronics module 30, in Automatic Mode, to cycle from IDLE state through its PROCESS mode until the anti-microbial solution reservoir 38 is full as electronically indicated by the float level sensor 39. The anti-microbial fluid combination outlet 33 is plumbed to the anti-microbial solution reservoir 38 by the anti-microbial reservoir inlet 40. Upon an external call signal from a CWE 37 to anode control module 41, the anti-microbial solution reservoir 38 will have stored anti-microbial solution expelled using an electronically actuated pump 42 which is electronically connected to the node control module 41 with signal wiring 44. The signal wiring 44 also electronically connects the node control module 41 to the CBWs 37 and the normally closed solenoid injection valves 43. The anti-microbial solution reservoir 38 is plumbed to the electronically actuated pump 42 using anti-microbial agent injection lines 45. Upon expulsion of the anti-microbial solution from the anti-microbial solution reservoir 38, the node control module 41 is programmed to actuate one of multiple normally closed solenoid injection valves 43 in order to be able to supply multiple CWEs with anti-microbial agent through the anti-microbial agent injection lines 45. In the case of CWE 37 system, the most effective integration of the present invention into the industrial laundry facility would be based on the time of injection, and would be to have the anti-microbial agent delivered into the CWE 37 during its final rinse cycle. In combination with electronic control and monitoring system software, the node control module 41 can be programmed, which allows the operator to fully program, and thus control, when the anti-microbial agent is delivered and how much of it is delivered.

Figure 13:
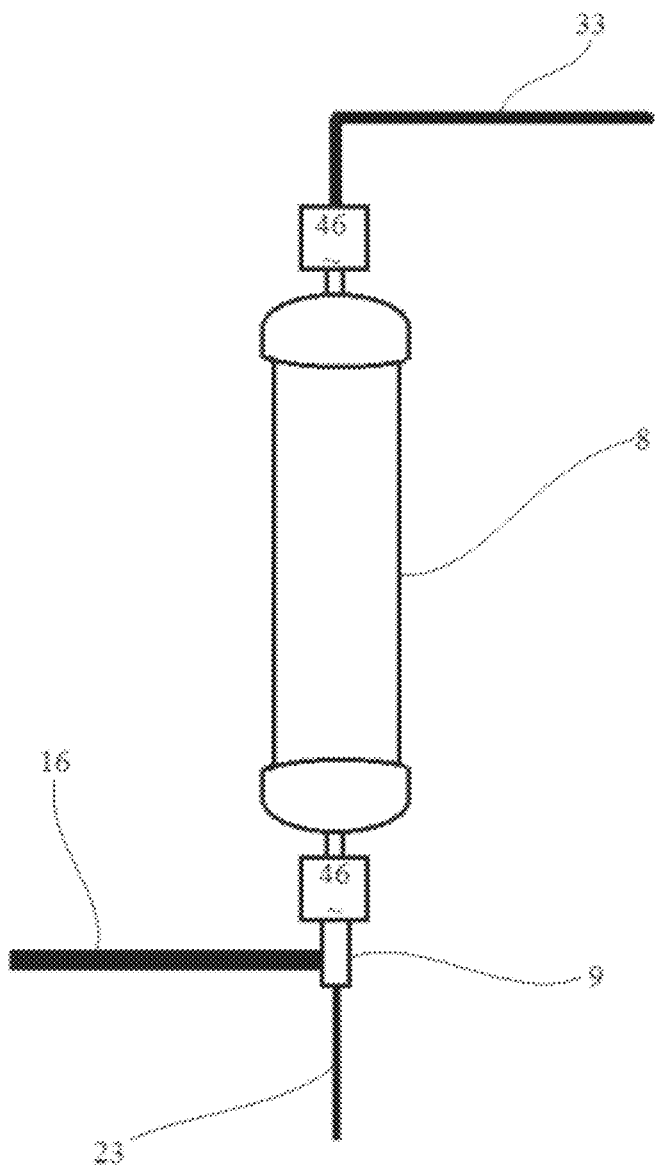

FIG. 13 shows a fluid microbial cleansing system comprised of six (primary elements of the embodiment in FIG. 5 of the present invention with the addition of a fluid evaluation system. Fluid #1 is carried to the fluid diffusion device 9 through the water line 16. Fluid #2 is carried to the fluid diffusion device 9 through the air line 23. The fluid combination forms inside the fluid diffusion device 9 and before entering the anti-microbial canister 8, the fluid combination is measured by a fluid evaluation device such as a resistivity sensor 46. Once the fluid combination exits the anti-microbial canister 8 and before it is delivered to its application through the anti-microbial fluid combination outlet 33, it is measured a second time by a second fluid evaluation device such as resistivity sensor 47. Resistivity readings from the sensors 46 and 47 are compared to determine the level of anti-microbial ions present in the fluid combination for microbial cleansing. By measuring and comparing resistivity or conductivity of the fluid combination before it enters the anti-microbial canister 8 and after it exits the anti-microbial canister 8, the effectiveness of the anti-microbial canister and the level of ion generation enhanced by the fluid diffusion device can be evaluated for use in specific applications.

PROPORTIONS AND APPROXIMATE DIMENSIONS OF THE EXAMPLE EMBODIMENTS

Proportions and approximate sizes for an example embodiment may be described with reference to the drawings. Referring to FIG. 1. The three components of the roll 4 have roughly equal width dimensions of about 18". The anti-microbial metallic coated substrate 1 has the largest length of about 50", the porous body 3 has the next largest length of about 36" and the support frame 2 has the shortest length of about 24". The thickness of the anti-microbial metallic coated substrate 1 is the smallest followed by the support frame 2 and finally the porous body 3 has the largest thickness. The thicknesses of the anti-microbial metallic coated substrate 1 and support frame 2 are less than 1/8". The thickness of the porous body 3 ranges from 1/8" and above.

Referring to FIG. 2 and FIG. 3, the diameter of the roll 4 is equal to the inside diameter of the central cylinder 5 as seen in FIG. 3. The length of the roll 4 is equal to the length of the inside of the central cylinder 5. The length of the anti-microbial canister 8 can range from approximately 6" to 36" but may be even larger in certain applications. The relationship roughly follows that for each GPM of water set to flow through the anti-microbial canister 8, 9" of central cylinder 5 length are ideal. The inlet end cap 6 and the outlet end cap 7 have inner diameters which are approximately equal to the outer diameter of the central cylinder 5 and an outer diameter which is slightly larger than that of the central cylinder 5.

Referring to FIG. 3 and FIG. 4, the cylindrical body of the fluid diffusion device 9 has a diameter which is less than or equal to the central cylinder 5. The diffuser 13 will have a diameter less than or equal to the cylindrical body of the fluid diffusion device 9. The diffuser 13 incorporates a barb 12 feeding air into a hollow porous diffusion material which resides inside the main body of the fluid diffusion device 9.

Referring to FIG. 5, the components which comprise the electronic control and monitoring system shown in FIG. 5 all mount onto the mounting surface 15 which has approximate width and length dimensions of 2'×4'. The water line 16 diameter can range from 1/4" tube to 2" tube. The anti-microbial canister 8, manual water shut off 17, the water pressure regulator 18, water filter 19, the solenoid water shut off valve 20, the water temperature sensor 21, the water pressure sensor 22, the flow reducer 28, and the flow sensor 29 will all be plumbed to appropriately connect in-line with the water line 13. The airline can range from 1/4" to 1" but the approximate diameter of the airline is 3/8". The fluid diffusion device 9 will have a barb 12, which will connect in-line with the air line 23. The liquid inlet and fluid combination outlet of the fluid diffusion device 9 will connect in-line with the water line 16. The air pressure sensor 24, the solenoid air shut off 23, and the air pressure regulator 27 will all be plumbed to appropriately connect in-line with the air line 23.

The anti-microbial solution reservoir 38 should have a large enough volume to at least supply a conventional washer-extractor with 10% of its rinse water volume instantaneously. 450 lb CWEs 37 use roughly 50 gallons of rinse water. This means that for a standard, 450 lb capacity CWE 37, the anti-microbial solution reservoir 38 must be a minimum of 5 gallons. For each conventional washer extractor that must be supplied with anti-microbial solution, at least another 5 gallons must be added to the total volume of the anti-microbial solution reservoir. For example, to supply 5 CWEs 37, at a minimum, the anti-microbial solution reservoir 38 would need to be 25 gallons. There is no size limitation to the ant-microbial solution reservoir 38 other than space constraints in the installation site.

MATERIALS USED IN THE EXAMPLE EMBODIMENTS

Referring again to FIG. 1, the metallic anti-microbial coated substrate 1 shall be a material containing a metallic anti-microbial agent such as copper or silver and be pliable enough to roll into the roll 4 shown in FIG. 2, in dimensions appropriate for and specific to a given implementation. In the example embodiment, the material employed for the coated substrate is a finely woven silver coated nylon cloth. The thickness of the silver coating on the nylon threads of this cloth can range from 100 nanometers to 10 microns in the example embodiment; an effective silver coating thickness has been found to be 500 nanometers (0.5 microns). The support frame 2 must be made of a material which is rigid enough when configured into the roll 4 and placed into anti-microbial canister 8 as shown in FIG. 3 to withstand the turbulated fluid combination flow experienced through the anti-microbial canister 8. The support frame 2 can be made from plastic or metal. In the example embodiment, the support frame 2 is a polyvinyichloride (PVC) grating. The porous body 3 must be able to allow sufficient fluid flow and be pliable enough to configure into the roll 4 seen in FIG. 2 and can be made from plastic, metal or foam. An effective material for the porous body has been found to be low density polyurethane (PU) foam.

The central cylinder 5, the inlet end cap 6, and the outlet end cap 7 seen in FIG. 3, which house the roll 4, must be strong enough under pressure to avoid fracture or rupture at fluid pressure levels specific to implementations in industrial laundry plants; in the current embodiment, this maximum fluid pressure level is 100 psi. The end caps and central cylinder 5 can be made from metal or plastic. An effective material found for the central cylinder 5, inlet end cap 6 and outlet end cap 7 is schedule 80 PVC.

The diffuser 13 seen in FIG. 4 which adds separate fluid to the fluid passing through the main body of the fluid diffusion device 9 should be made of a porous metal or plastic in order to avoid fracture under pressure while allowing the diffusing action through its walls. The fluid diffusion device 9 main body should also be made of metal or plastic. An effective material found for the entire fluid diffusion device 9 including the barb 12 and diffuser 13 is stainless steel.

The mounting surface 15 should be made of metal, wood, or plastic in order to hold the mounted components seen in FIG. 5. The water line 16 should be made of corrosion resistant metal or plastic in order to withstand implementation and industrial laundry plant pressure without rupture. The air line 23 should be made of plastic or corrosion resistant metal in order to withstand implementation and industrial laundry plant pressure without rupture. All of the mechanical devices should be made of durable plastic such as polytetrafluoroethylene (PTFE) or metal; effective metals are stainless steel or aluminum to avoid silver cementation and corrosion. The electronic devices should have valve components made from rigid plastic in order to withstand frictional breakdown due frequent rubbing during on/off cycles.

The anti-microbial solution reservoir 35 should be made of a durable light-resistant polymer in order to avoid cementation and/or deterioration of the anti-microbial solutions during temporary storage.

OPERATION OF THE INVENTION

To explain the operation of the present embodiment of the invention, the fluid motion through the various components along with the electronic control and monitoring of these fluids must be understood.

Many combinations of fluids (in their liquid or gaseous states) and materials are capable of creating effective anti-microbial treatments; water, air, and the combination of the two, referred to as the fluid combination, will be the three fluids described because of their use in the current embodiment of the invention. The metallic anti-microbial material described will be the previously cited silver coated nylon cloth. The following method description employs this specific set of fluids and materials which have been shown to produce effective anti-microbial treatment. Because specifics of the electronic control and monitoring system have been previously described in detail, the focus of this section will be on the materials science behind how the anti-microbial solution is generated.

Power is supplied to the electronics module 30. System INITIALIZATION begins. The manual water shut off valve 14 must be turned to the open position. Both of the electronic solenoid valves begin in the off position. Once timing and basic parameters are confirmed by the electronic control and monitoring system, IDLE state is established. The electronics module 30 has two modes by which to advance from IDLE state to PROCESS mode. Those modes are: Manual Mode and Automatic Mode. Manual mode uses the Start button and Stop button on the electronics module 30, at the command of the operator, in order to cycle the system through PROCESS mode, whereas Automatic Mode relies upon an external signal to cycle the system through PROCESS mode. In the case of integration into a CBW system, the external signal would come from the CBW computer control system. In the case of integration into a CWE system, the external signal would be transmitted from the float level sensor 36. Both PROCESS cycles of the electronic control and monitoring system are identical, and follow the flow diagram depicted in FIG. 6 and are detailed fully in supplementary FIGS. 7, 8, 9, and 10. They function as follows: The solenoid air shut off valve 26 is opened by electronic command of the electronics module 30. The electronics module 30 electronically commands the solenoid air shut off valve 26 to open before the electronics module 30 electronically commands the solenoid water shut off valve 20 to open. At this point, air from the pressurized air source 32 flows through the air pressure regulator 27, regulated to between 30 psi and 60 psi. This allows air to preload its flow through the air line 23 and continuously through the fluid diffusion device 9. Air enters the barb 12 and then enters the diffuser 13 and permeates the diffuser 13. After the programmed pause, the electronics module 30 electronically commands the solenoid water shut off valve 23 to open. Water entering the solenoid water shut off valve 20 from the hot water source 31 at between 120° F. and 170° F. is regulated to between 20 psi and 50 psi by the water pressure regulator 18. Different embodiments of the invention will have different ratios of fluid #1 to fluid #2; in the current embodiment, the flowing water pressure to flowing air pressure ratio is 4:5. The electronics module 30 then receives a water flow-rate reading from the flow sensor 29. It also receives readings from the water temperature sensor 21, water pressure sensor 22, and air pressure sensor 24. If the water flow rate, water temperature, water pressure, and air pressure are all reading within the programmed parameters then system PROCESS continues and the electronics control and monitoring system continues until an event sends the system back into IDLE state or SHUTDOWN sequence as shown in FIG. 6. If the water flow rate, water temperature, or water pressure readings are outside the programmed parameters then the electronics module 30 logs the event data to non-volatile memory, transmits the data through the local area network and alerts the operator. The electronics module 30 goes into a standby status until a command from the operator is received. At this point in the PROCESS sequence of the current embodiment, anti-microbial solution generation begins.

Upon the meeting of air through the diffuser 13 and water passing over the outside of the diffuser 13 as the water passes through the main body of the fluid diffusion device 9, the two fluids mix to form the fluid combination. The fluid combination is a water and air mixture. The maximum amount of gaseous oxygen from the air is dissolved into the water. The high dissolved oxygen level in the fluid combination makes the fluid combination corrosive. This corrosive behavior corrodes small amounts of the silver coating off of the silver coated nylon cloth 1 when the fluid combination comes in contact with the inside of anti-microbial canister 8, more specifically, the roll 4 inside the anti-microbial canister 8. The dissolved oxygen in the fluid combination reacts with the surface of the silver coated nylon cloth to form soluble silver oxides. These oxides dissolve, resulting in ionic silver in aqueous solution and oxygen free to form gaseous molecules or other compounds. The porous body 3 prevents laminar flow through the anti-microbial canister 8; it channels the fluid combination all throughout the layers of roll 4 inside of the anti-microbial canister 8 to promote even wear of the silver coated nylon cloth during the corrosion process. The fluid combination flows generally from inlet end cap 6 to outlet end cap 7 and exits through the water flow reducer 25 and flow sensor 29. The placement of the flow reducer 28 after the anti-microbial canister 8 in the system allows for the highest possible fluid pressure in the anti-microbial canister 8. This high fluid pressure is desired in order to keep the available oxygen dissolved in the fluid combination. The electronics module 30 takes a flow reading at the flow sensor 29 after it receives the pressure reading from the air pressure sensor 24. If the fluid combination flow through the flow sensor 29 is within the specified parameters then system PROCESS mode continues and the electronics module 30 continues to run PROCESS mode until an event occurs. If the flow rate is outside the specified parameters then the electronics module 30 the event data to non-volatile memory, transmits the data through the local area network and alerts the operator. The run sequence actively monitors transmissions delivered to the electronics module 30 from the 3 sensors and logs these transmissions to a non-volatile internal storage device and also optionally off site through the local area interact connection. Upon exiting the flow sensor 29 the fluid combination now contains dissolved ionic and nano-particle silver. In the case of CBW integration, the anti-microbial agent is delivered directly into the CBW rinse module 33. In the case of CWE 37 integration, the anti-microbial agent is temporarily stored in the anti-microbial solution reservoir 38 until the conventional CWE electronically signals the node control module 41 to trigger the electronically actuated pump 42 to turn on and the solenoid injection valves 43 to open, thereby forcing anti-microbial agent through the anti-microbial agent injection lines 45.

At this point the silver-containing fluid combination is a liquid anti-microbial agent ready to treat linens, surfaces, or other fluids in order to provide lasting anti-microbial treatment. The lasting effect is brought on by the residual tendency of silver and because silver is a heavy metal which behaves according to the Oligodynamic Effect. The electronics module 30 can be programmed to allow different combinations of temperature, air pressure, water pressure, and flow to adjust the corrosive properties of the fluid combination. By adjusting the level of corrosiveness, the silver concentration of the anti-microbial agent can be controlled. Using the previously cited effective set of materials and fluids, the anti-microbial device can be controlled to selectively produce aqueous ionic silver solutions ranging in concentration from 1 part per (ppb) to approximately 700 parts per billion (ppb) for example embodiments. The more corrosive the fluid combination is, the higher the silver concentration will be. The higher the silver concentration is in the anti-microbial agent, the stronger the anti-microbial effects will be and the longer they will last. Therefore, the present invention can be programmed to produce varying levels of anti-microbial treatment. One example of anti-microbial treatment is represented by FIG. 11, where the anti-microbial agent is delivered to an industrial CBW. The fine dispersion of silver ions and agglomerated silver particles which are corroded from the surface of the silver coated nylon cloth 1 while rolled in the roll 4 are what provide the anti-microbial properties of the anti-microbial agent in this example. The residual tendency of the fine silver dispersion provides the lasting anti-microbial effects.

Implementation Example 1

In studies for efficacy in determining silver ion concentration levels for impregnating fabric in laundry cycles, a 10 gallon bath simulating a washer rinse capacity was infused with silver ions at a concentration of 50 ppB and loaded with 1.5 kg of bed linen. A soak time of 2 minutes and 30 seconds was allowed and the linen removed and dried. Measured concentration level of ionic silver of 1.7 μg/kg of linens was obtained.

Implementation Example 2

For measurement of anti-microbial benefits to industrial laundry processes, the elements represented in FIG. 5 combined with those represented in FIG. 12 as described previously were assembled in an example implementation of the present invention into a CWE process that yields healthcare linens with desired silver content by weight for anti-microbial behavior in the linen.

Water as fluid #1 regulated to 38 psi, 150° F., flowing at 1 gpm and air as fluid #2 regulated to 47 psi flowing through the described embodiment produced anti-microbial solutions with ionic silver concentrations of between 160 ppb and 240 ppb. The anti-microbial solutions were stored in the anti-microbial reservoir during a CWE wash cycle. At the onset of the rinse cycle in the CWE containing 205 kg of healthcare bed linen, 60 gallons of anti-microbial solution was injected into the CWE from the reservoir. The anti-microbial solution was exposed to the 205 kg toad of healthcare bed linen for 2 minutes and 50 seconds before the CWE drained and extracted the anti-microbial solution.

After the healthcare bed linen was dried and folded in the industrial process, samples were collected and analyzed for silver content by weight of healthcare bed linen. The treated linens contained an ionic silver concentration of 0.17 μg/kg of healthcare bed linen.

Having now described the invention in detail as required by the patent statutes, those skilled in the art will recognize modifications and substitutions to the specific embodiments disclosed herein. Such modifications are within the scope and intent of the present invention as defined in the following claims.

What is claimed is:

1. An antimicrobial device comprising:
- a metallic coated substrate;
- a porous body positioned with respect to the substrate for intimate contact of turbulated fluid in the porous body with the substrate;
- a support frame intermediate the substrate and porous body to support the metallic coated substrate adjacent the porous body;
- a housing containing the substrate, support frame and porous body and having an inlet and outlet for the fluid, said substrate, support frame and porous body positioned for flow of the fluid through the porous body from inlet to outlet;
- a fluid diffusion device containing hollow porous diffusion material connected upstream of the housing inlet and having fluid inlets for a first fluid and a second fluid creating a corrosive fluid for turbulation in the porous body; and,
- an electronic control and monitoring system including an electronic module programmed to adjust the corrosive properties of the combination of the first fluid and second fluid by controlling flow of the first and second fluids received by the fluid diffusion device for varying concentration of metallic ions dissolved into solution from the substrate between 1 ppb and 700 ppb.

2. The antimicrobial device defined in claim 1 wherein the housing is a cylindrical canister and the metallic coated substrate, support frame and porous body are helically rolled within the canister.

3. The antimicrobial device defined in claim 2 wherein the metallic coating of the substrate is silver.

4. The antimicrobial device defined in claim 3 wherein the first fluid is water and the second fluid is air and the electronic control and monitoring system includes:
- a fluid pressure regulator connected to the fluid diffusion device water inlet,
- an air pressure regulator connected to the fluid diffusion device air inlet; and
- a flow reducer connected to the outlet of the housing.

5. The antimicrobial device defined in claim 4 wherein the electronic control and monitoring system further comprises:
- a solenoid fluid shut off valve connected upstream of the fluid pressure regulator;
- a temperature sensor for incoming water;
- a fluid pressure sensor for incoming water;
- an air pressure sensor for incoming air;
- a solenoid air shut off valve connected upstream of the air pressure regulator; and
- a flow sensor connected downstream of the flow reducer.

6. The antimicrobial device defined in claim 5 wherein the electronic module is connected to the temperature sensor, fluid pressure sensor, air pressure sensor and flow sensor for data input, said electronic module adapted for operation of at least the solenoid fluid shut off valve and solenoid air shut off valve as programmed to adjust corrosive properties responsive to the data input.

7. The antimicrobial device as defined in claim 6 wherein the electronic module as programmed to adjust the corrosive properties has program states including an initialization state, an idle state, a process state and a shut down state, said electronic module implementing the program states responsive to the data input and said program states determining operation of at least the solenoid fluid shut off valve and solenoid air shut off valve.

8. The antimicrobial device defined in claim 1 further comprising:
a first fluid evaluation device at the housing inlet; and
a second fluid evaluation device at the housing outlet.

9. A method for antimicrobial treatment of a fluid comprising:
positioning a metallic coated substrate in a support frame for intimate contact with a porous body positioned with respect to the substrate for intimate contact of turbulated fluid in the porous body with the substrate, said support frame intermediate the substrate and porous body to support the metallic coated substrate adjacent the porous body;
directing fluid via a housing containing the substrate, support frame and porous body with an inlet and outlet for the fluid, said substrate, support frame and porous body positioned for flow of the fluid through the porous body from inlet to outlet;
aerating the fluid with a fluid diffusion device containing hollow porous diffusion material connected upstream of the housing inlet and having fluid inlets for a first fluid and a second fluid creating a corrosive fluid to provide a turbulated fluid at an inlet to the housing for turbulation in the porous body to produce a selected concentration of metallic ions in the fluid at an outlet of the housing;
programming an electronic control and monitoring system including an electronic module to adjust the corrosive properties of the combination of the first fluid and second fluid by controlling flow of the first and second fluids received by the fluid diffusion device for varying concentration of metallic ions dissolved into solution from the substrate between 1 ppb and 700 ppb and,
providing the fluid from the outlet of the housing for antimicrobial action.

10. The method of claim 9 wherein the metallic ions are silver and the selected concentration of metallic ions is between 50 and 700 parts per billion (ppb).

11. The method of claim 10 wherein the concentration of silver ions is between 50 ppb and 500 ppb.

12. The method for antimicrobial treatment of fluid as defined in claim 9 further comprising:
providing power to a controlling electronics module and performing an initialization sequence;
if the initialization is successful entering an idle state;
selecting a manual mode or automatic mode;
in automatic mode, upon receiving an external signal advancing from idle state to a process mode or in manual mode, advancing from idle state to process mode upon receiving a start button command, said process mode performing the steps of directing the fluid, aerating the fluid and providing the fluid;
if a power failure occurs, entering a shutdown sequence;
upon receiving a process complete command in automatic mode or a stop button command in manual mode, returning from process mode back to idle state; and,
if the shutdown sequence is complete, upon restoring power, return to the initialization sequence.

13. The method for antimicrobial treatment of fluid as defined in claim 10 wherein
the step of directing fluid comprises providing water at a predetermined flow rate, temperature and pressure, and
the step of aerating comprises providing regulated air at a predetermined pressure for turbulation of the water flowing through the housing to provide an anti-microbial solution with ionic silver concentrations of between 50 ppb and 240 ppb and,
the step of providing the fluid comprises providing the water to a commercial washing system to provide ionic silver concentration in linens washed in the commercial washing system at between 0.17 µg/kg and 1.7 µg/kg.

14. An antimicrobial device comprising:
a water pressure regulator connected to a hot water source;
an air pressure regulator connected to an air inlet;
a diffusion device containing hollow porous diffusion material having an inlet connected to receive water from the water pressure regulator, an inlet connected to receive air from the air pressure regulator and an outlet;
a metallic coated substrate;
a porous body positioned with respect to the substrate for intimate contact of turbulated water in the porous body with the substrate;
a support frame intermediate the substrate and porous body to support the metallic coated substrate adjacent the porous body;
a housing containing the substrate, support frame and porous body and having an inlet connected to the diffusion device outlet and an outlet for the water, said substrate, support frame and porous body positioned for flow of the water through the porous body directly from housing inlet to housing outlet;
a flow reducer connected to the outlet of the housing; and,
an electronics module programmed to control the water pressure regulator, air pressure regulator and flow reducer to adjust corrosive properties of the combination of the water and air thereby varying concentration of metallic ions dissolved into solution in the water from the substrate between 1 ppb and 700 ppb.

* * * * *